United States Patent [19]

Rotteveel et al.

[11] Patent Number: 5,669,389
[45] Date of Patent: Sep. 23, 1997

[54] ENDOSCOPIC PROBE

[75] Inventors: Bart Joseph Rotteveel, Delft, Netherlands; Pieter Derk Brommersma, Hamburg, Germany

[73] Assignee: B.V. Optische Industrie "De Oude Delft", Delft, Netherlands

[21] Appl. No.: 969,210

[22] PCT Filed: Jul. 31, 1991

[86] PCT No.: PCT/NL91/00142

§ 371 Date: Feb. 22, 1993

§ 102(e) Date: Feb. 22, 1993

[87] PCT Pub. No.: WO92/02179

PCT Pub. Date: Feb. 20, 1992

[30] Foreign Application Priority Data

Aug. 2, 1990 [NL] Netherlands ............... 9001755

[51] Int. Cl.$^6$ .................................................. A61B 8/12
[52] U.S. Cl. .................. 128/662.06; 128/660.08; 128/663.01
[58] Field of Search ............... 128/662.06, 660.08, 128/660.09, 663.01, 660.1, 4

[56] References Cited

U.S. PATENT DOCUMENTS

| | | | |
|---|---|---|---|
| 3,805,213 | 4/1974 | Austin | 361/749 |
| 3,936,791 | 2/1976 | Kossoff | 128/663.01 |
| 4,543,960 | 10/1985 | Harvi et al. | 128/662.06 |
| 4,549,533 | 10/1985 | Cain et al. | 128/663.01 |
| 4,787,247 | 11/1988 | Wuchinich et al. | 128/660.1 |
| 4,834,102 | 5/1989 | Schwarzchild et al. | 128/662.06 |
| 4,974,590 | 12/1990 | Saito | 128/662.06 |
| 5,127,410 | 7/1992 | King et al. | 128/662.03 |
| 5,176,142 | 1/1993 | Mason | 128/662.06 |

*Primary Examiner*—Richard J. Apley
*Assistant Examiner*—John Mulcahy
*Attorney, Agent, or Firm*—Louis E. Marn

[57] ABSTRACT

Endoscopic probe in particular suitable for use as a TEE-probe, comprising a flexible tube having at one end a probe head which is provided with ultrasonic transducer means of the phased array type with a transducer made up of a number of elongated transducer elements which elements can be individually electrically controlled by means of cables connected to the individual elements and extending through the flexible tube in which the transducer is mounted in an essentially cylindrical transducer housing which is placed in a cavity in the probe head and is rotatable about a longitudinal axis extending at right angles to the longitudinal axis of the probe head, by means of drive means interacting with the transducer housing while the elongated transducer elements are connected by means of flexible conductors to the cables extending through the flexible tube and in which the cavity in the probe head is sealed with an acoustically transparent head and the transducer is coupled acoustically to the fixed cap by means of acoustic coupling means which permit a rotation of the transducer relative to the fixed cap.

22 Claims, 4 Drawing Sheets

5,669,389

1

ENDOSCOPIC PROBE

BACKGROUND OF THE INVENTION

(1) Field of the Invention

The invention relates to an endoscopic probe, in particular suitable for use as a TEE probe.

(2) Brief Description of the Prior Art

An endoscopic probe is known from the article "An endoscopic micromanipulator for multiplanar transesophageal imaging" by Roy W. Martin et al. in Ultrasound in Med & Biol., Vol. 12, No. 12, pp. 965–975, 1986. The known probe has a probe head with a slightly flattened part containing an essentially flat transducer made up of a number of individual adjacent elongated elements of piezoelectric material which can be excited individually, and which together form a phased array. By exciting the strip-type elements in a suitable sequence, it is possible to obtain a beam which scans the environment to be examined and produces reflections in a plane lying at right angles to the elongated elements, as described in greater detail by J. C. Somer in "Echocardiography", N. Bom, published by Martinus Nijhof in The Hague, 1977. Rotating the flexible tube, and thus the probe head, about the longitudinal axis means that the environment around the probe head can be scanned by an ultrasonic beam. Pulling cables also extend through the flexible tube, by means of which said head can be pulled forwards or backwards.

In the medical world there is a need for an endoscopic probe with which more information can be obtained. In the past it was proposed that a biplane TEE probe should be used for this purpose. Such a probe head has two transducer arrays lying one after the other in the lengthwise direction of the flexible tube and the head, each again composed of adjacent elongated elements. The elements of one transducer extend at right angles relative to the elements of the other transducer. With this head it is therefore possible to obtain two scanning beams which can carry out a scanning movement in directions extending at right angles to each other.

A disadvantage of this known probe is that the scanning beams originate in two different points. Another disadvantage is that the rigid head is relatively long, which can lead to problems in practical use. Two separate transducer arrays with the same definition per array also require twice the number of control cables, which all have to be conveyed through the flexible tube. However, the flexible tube has little or no space for these.

In order to eliminate these problems, it was proposed in U.S. Pat. No. 4,543,960 that the transducer array should be fitted in the probe head so that it is rotatable about an axis extending at right angles to the plane of the array. For this, a transducer housing, bearing the transducer, array and rotatable about a pin provided on the side of the transducer housing facing away from the array, is fitted in a cavity in the probe head. The elements of the transducer array are connected by means of conductors formed on two flexible printed circuit boards to the different cores of one or more electrical cables extending through the flexible tube. The flexible printed circuit boards lie coiled around the transducer housing.

It is not indicated in U.S. Pat. No. 4,543,960 whether, and if so in what way, the cavity in which the transducer housing with the transducer is situated is sealed off relative to the environment. A good seal with as few seams and crevices as possible is, however, necessary from the point of view of hygiene if the probe is intended for repeated use.

2

The object of the invention is therefore to provide an endoscopic probe which meets the above mentioned requirement, and more generally to provide a reliable endoscopic probe which is suitable for repeated use on different patients, which is easy to clean externally, and by which the human body can be examined internally by echography in the optimum manner.

SUMMARY OF THE INVENTION

For this, according to the invention an endoscopic probe of the above-described type is characterised in that the cavity in the probe head is sealed with an acoustically transparent head and the transducer is coupled acoustically to the fixed cap by means of acoustic coupling means which permit a rotation of the transducer relative to the fixed cap.

BRIEF DESCRIPTION OF THE DRAWINGS

The invention will be described in greater detail below with reference to the appended drawing of a number of examplary embodiments.

DETAILED DESCRIPTION OF THE INVENTION

Figure 1:
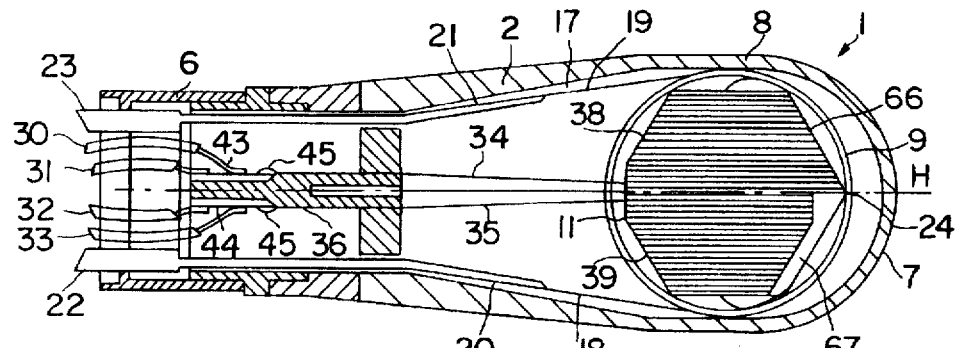
FIG. 1 shows schematically a cut-away top view of an examplary embodiment of a probe head of a TEE probe according to the invention.
Figure 2:
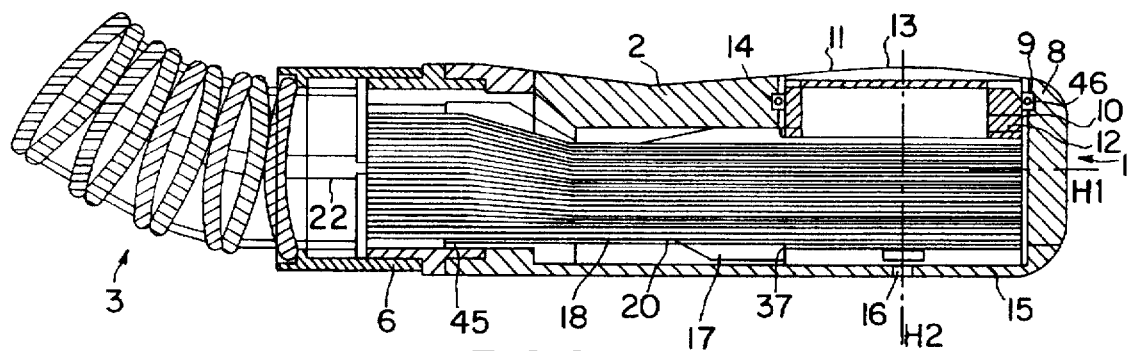
FIG. 2 shows schematically a cut-away side view of the probe head of FIG. 1.
Figure 3:
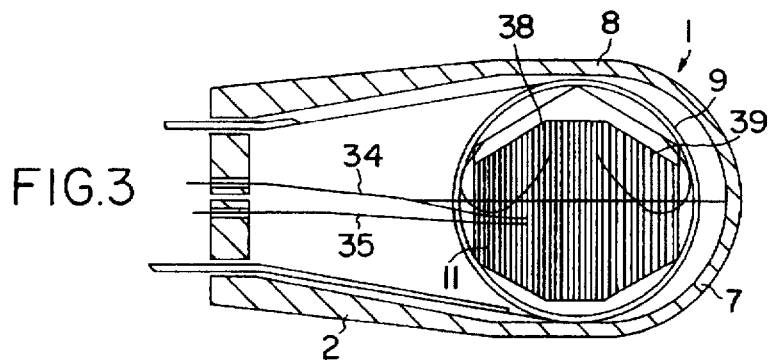
FIG. 3 shows schematically a top view of the probe head of FIG. 1, in a different working position.

FIGS. 1 to 3 show a TEE probe as an example of an embodiment of the invention. A TEE (trans esophageal echocardiography) probe is a device which can be used to examine the heart, or other parts of the body in the region of the esophagus, by ultrasonic radiation from the esophagus through the esophagus wall. The probe shown comprises a probe head 1 with a housing 2, which connects to a flexible end part 3 of a flexible tube which is not shown. Using Bowden cables 4, 5 extending through the flexible tube, the probe head can be bent forwards (as shown in FIG. 2) or backwards. This movement is made possible by the end part 3. If desired, similar Bowden cables which permit a sideways swing of the probe head can be present.

The housing 2 connects by means of a connecting piece 6 with round cross-section to the end part 3 of the flexible tube, but itself has an essentially rectangular cross-section with rounded edges which widens out slightly to a holder 8 which is shut off at the free end by a semicircular wall 7 and in which an ultrasonic transducer of the phased array type is placed. The holder 8 is provided with a circular aperture 9 in an essentially flat top wall. Situated in and behind the aperture is the transducer which, as can be seen in FIG. 2, comprises an essentially flat transducer 11 lying on a backing layer 10. The transducer 11 is made up of a number of adjacent, but separate strip-type transducer elements which can be for example, piezoelectric elements, and which in the situation shown in FIG. 1 extend, parallel to the longitudinal axis H of the probe head. The backing layer absorbs ultrasonic vibrations which are radiated towards the interior of the probe head and which, if not absorbed, would lead to disturbing reflections. The backing layer 10 is confined inside an electrically insulating frame 12 which can be made of, for example, a suitable plastic.

Above the array 11 is an acoustic lens 13, which will be described in greater detail below. In a suitable manner phasedly exciting the individual strip-type transducer elements makes it possible to obtain an ultrasonic beam which can scan an area the shape of a sector of a circle in a plane at right angles to the strip-type elements. This technique, which is known per se, can therefore be used to scan the environment of the probe head with a swinging beam, but the swing can take place in only one plane.

The lens 13, the transducer 11, the frame 12 and the backing-layer 10 are placed in a transducer housing 14 which is an essentially cylindrical shape. The transducer housing 14 is sealed at the level of the aperture 9 by the lens 13, and in the example shown also has a bottom 15 which is supported on a pin 16 fitted in a bore in the wall of the housing of the probe head opposite the aperture 9. The central axis of the pin coincides with the central axis H2 of the transducer housing and the centre point of the circular opening lies on said central axis H2, so that the transducer housing is rotatable about the pin. In the examplary embodiment shown, the transducer housing is rotatable from the rest position shown in FIG. 1 both clockwise and anticlockwise through approximately 90 degrees. FIG. 3 shows the probe head with the transducer 11 rotated through 90 degrees. The total rotation range is therefor 180 degrees, which means that a spatial area the shape of a sector of a sphere can be scanned completely with one and the same disc-type transducer made up of strips, without changing the position of the probe head itself.

In order to make the transducer housing 14 rotate, a belt 17 is passed around the transducer housing, the two free ends 18, 19 of which belt are connected to pulling cables 20, 21. The pulling cables are again in the form of Bowden cables, the outer cables of which are shown at 22, 23 The belt 17 can be a spring steel belt which is connected at one point, for example by a single spot weld, to the transducer housing 14. The connection in the rest position is on or near the longitudinal axis H1 of the probe head, as shown at 24 in FIG. 1, and FIG. 4.

Figure 4:
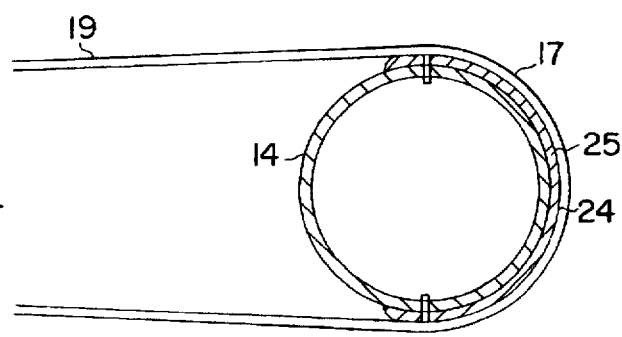
FIG. 4 shows a detail of the probe of FIG. 1 and FIG. 2.

All this is shown again in FIG. 4. An interposed metal strip is indicated by 25 and is connected in a suitable manner to the transducer housing. This prevents the pulling belt from slipping over the transducer housing.

For the electrical connection between the transducer elements and the electrical cables passed through the flexible tube, use is made of a flexible printed circuit board on which conductor tracks, connected at one side to the individual transducer elements and at the other side to the cores of the electric cable, are provided.

A number of cables are indicated by 30–33 in FIG. 1. The flexible printed circuit board is indicated by 34, 35. The flexible printed circuit board extends from a supporting plate 36 situated in the part of the probe head 1 connecting to the flexible tube and reaches into the transducer housing 14. For this purpose, the transducer housing is provided with a recess 37 extending through approximately 180 degrees along the periphery and being the height of the width of the flexible printed circuit board. Fitted in the transducer housing 14 under the backing layer are two pins 38, 39 which are fixed on the bottom 15 and/or in the backing layer 10. A strip of the flexible printed circuit board is passed around each of the pins 38, 39. Each strip extends in a loop under the backing layer towards connecting electrodes fitted on one end of the striptype transducer elements. The flexible printed circuit boards thus do not take up any space round the transducer housing.

In the examplary embodiment shown, the connecting electrodes for all strip-type elements are on the front side of the probe head. It is, however, also possible, for example, to fit the electrodes for the even-numbered elements on the front side and the electrodes for the odd-numbered elements on the opposite side of the transducer.

The pins 38, 39 are preferably placed in such a way that the flexible printed circuit boards extend essentially through the axis of rotation H2 of the transducer housing not only in the rest position shown in FIG. 1, but also on rotation of the transducer housing. Rotation of the transducer housing 14 therefore does not lead to a change in the space required for the flexible printed circuit boards. The parts of the flexible printed circuit boards extending outside the transducer housing-change position only to a very small extent during rotation of the transducer housing, as can be seen from a comparison of FIGS. 1 and 3.

The pins 38, 39 can be positioned as shown on both sides of the longitudinal axis H just past the centre line extending at right angles to the longitudinal axis.

The supporting plate 36 in this example bears on both sides printed circuit boards 43, 44 with conductor tracks to which the ends of the cables 30 to 33 are connected. The connecting point between the conductors of the printed circuit boards 43, 44 and the conductors of the flexible printed circuit board is indicated at 45.

Figure 5:
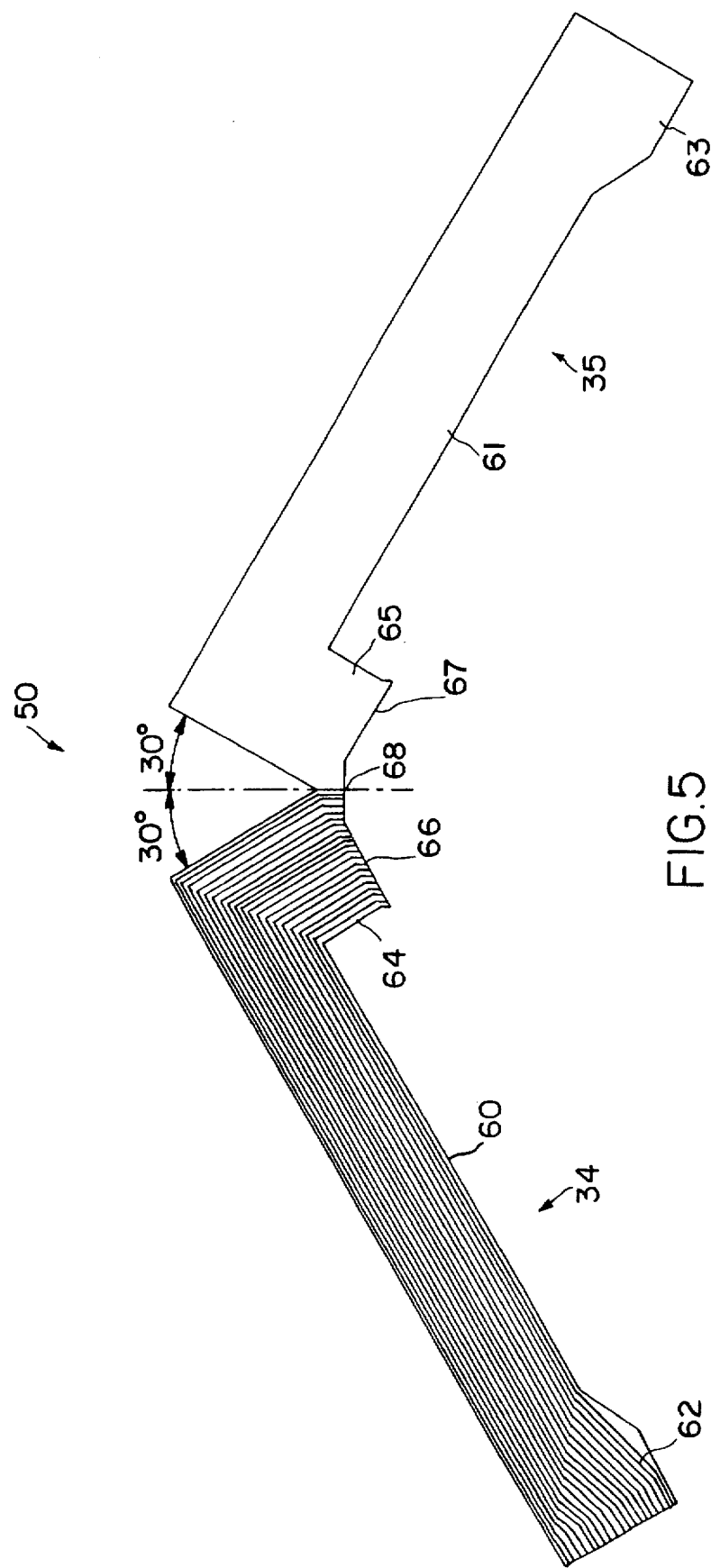
FIG. 5 is an example of a special printed circuit board which can be used in a probe according to the invention.

FIG. 5 shows schematically a flat blank of a flexible printed circuit board 50 which can be used in the device described. The printed circuit board shown has two wing strips 34, 35 which together form an approximately V-shaped flat blank. Each wing 34, 35 has an elongated part 60, 61 which has a first end 62, 63 for connection to the printed circuit boards 43, 44. Each wing also has a short transverse part 64, 65 which in the fitted state rests against the frame 12 at the front side (in FIG. 1 or FIG. 2). The transverse parts each have an end strip 66, 67. The end strips of the two transverse parts are connected to each other at 68, and thus form the connection between two wing strips. The end strips in the fitted state are folded over approximately at right angles, and at the bottom side lie against the connecting electrodes of the transducer elements. The connecting electrodes can be, for example, gold electrodes, and the connection can be made with conducting adhesive.

It is pointed out that the width of the elongated parts of the wing strips of the flexible printed circuit board described together with the thickness required for the backing layer largely determines the minimum height of the probe head. According to a further development of the idea of the invention, the elongated parts 60, 61 in the fitted state are folded double about a fold line extending in the lengthwise direction.

Figure 6:
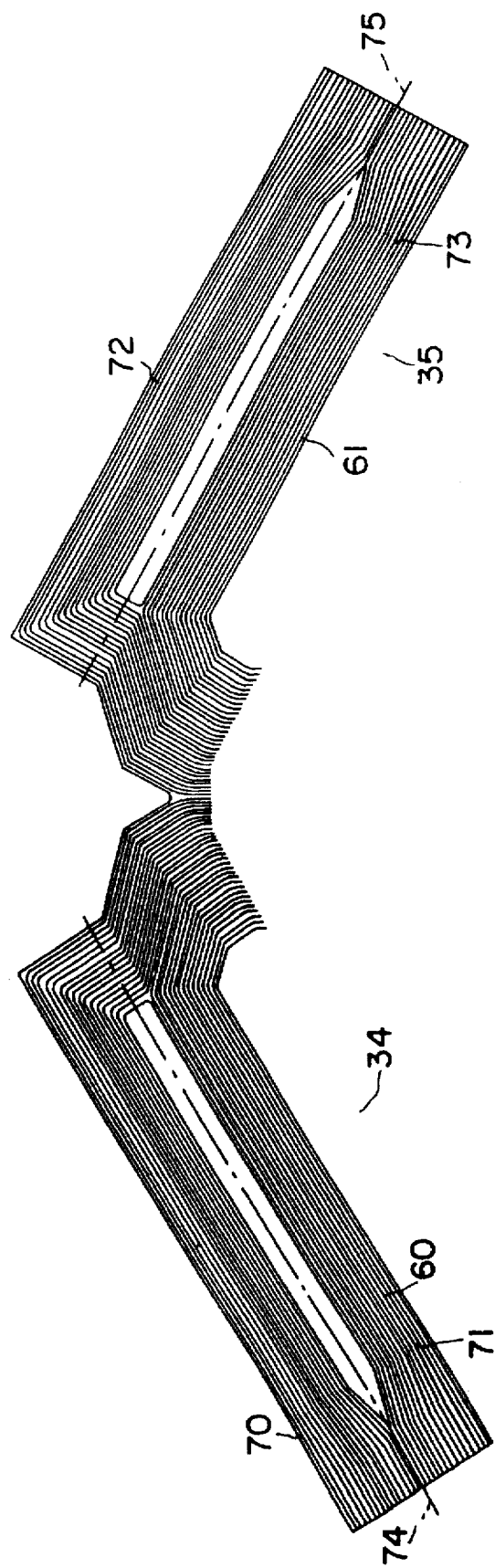
FIG. 6 shows a modification of the printed circuit board of FIG. 5.

An example of a flat blank for a flexible printed circuit board used for this purpose is shown in FIG. 6. The conductor tracks extending in the lengthwise direction of the elongated parts 60, 61 of the wing strips 34, 35 of the flexible printed circuit board are in each case divided into two groups 70, 71 and 72, 73 lying on both sides of a fold line 74, 75. The height required for the flexible printed circuit board is thereby greatly reduced.

When a flexible printed circuit board with double-folded elongated parts of the wing strips is used, if one or more printed circuit boards 43, 44 are again used for the connecting elements between the flexible printed circuit board and the cables 30 to 33, the printed circuit board 43 and/or 44 can be provided with conductor tracks on both sides. In this case each side of a printed circuit board 43 or 44 can, for example, correspond to one of the parts 70 to 73.

In principle, two (or more) individual flexible printed circuit boards could also be used. The use of a single printed circuit board sides the advantage that the position of the tracks, in particular in the end strips, is determined accurately. With the correct selection of the centre-to-centre distance of the tracks these can also be placed accurately in line with the gold electrodes of the transducer elements and, after correct positioning of a printed circuit board, a shifting of any second printed circuit board cannot take place.

Figure 7:
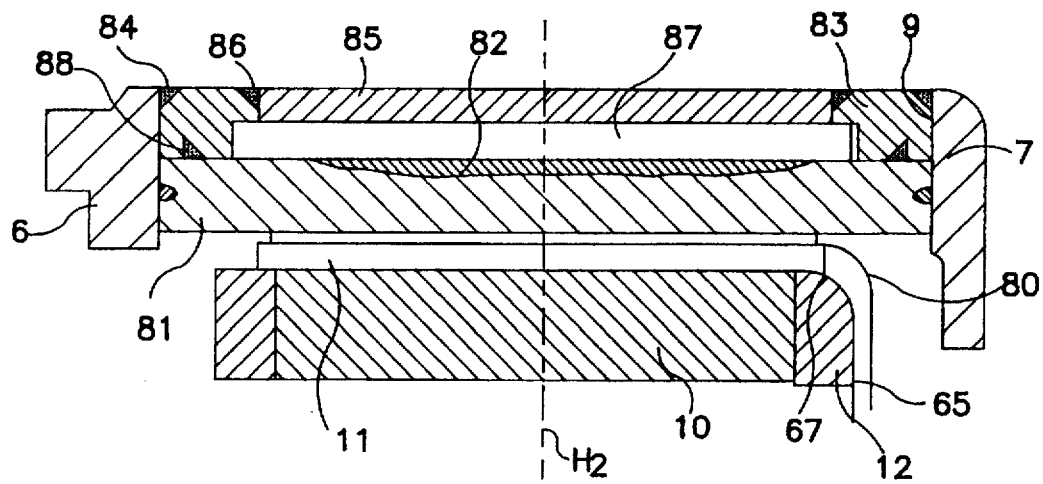
FIG. 7 shows schematically a first exemplary embodiment of a seal of the probe head of a probe according to the invention.

FIG. 7 shows schematically in longitudinal section a part of a probe head of an endoscopic probe according to the invention. The ultrasonic transducer 11 of the phased array type is shown. The transducer again lies on the backing layer 10 which is situated inside the frame 12. The transducer is connected in the manner already described at the front side and at the bottom side to the end strip 67 of the transverse part 65 of the flexible printed circuit board. An earth connection, connected at 80 to the top side of the transducer, is also shown.

A hard concave acoustic lens 81 which rotates along with the transducer is fitted on the transducer and can be, for example, glued on the transducer. The concave lens can be an acrylic lens or an anamorphotic type of lens made of hard epoxy resin. The lengthwise direction of the cavity corresponds to that of the individual elements of the transducer. The cavity of the lens in the example shown is filled with a so-called flat filler 82 which together with the lens forms a plane-parallel unit. The use of a flat filler is not, however, strictly necessary. A suitable screening foil, for example of aluminium capton™ (polyimide) can also be placed between the flat filler and the concave acoustic lens. The lens fits preferably in a sealing manner with its peripheral edge in the aperture 9 of the probe head. If desired, the lens can be provided along the peripheral edge with an O-ring, as indicated at 89. Fitted above the lens in the aperture 9 is a ring 83, which is fixed in the aperture 9 in a sealing manner, e.g. by gluing, as indicated at 84. An ultrasonic sound-transmitting cap 85 is fitted, also in a sealing manner, in the ring 83. The cap 85 is preferably made of hard material such as methylpentene copolymer silicone rubber, and in the example shown is glued to the ring 83, as indicated schematically at 86. The ring 83, which can be made of, e.g. glass ceramic material, lies with the bottom axial plane against the lens 81. Between the cap and the lens is a chamber 87 which along the periphery is bounded by the ring 83 and which is filled with an electrically non-conducting degassed fluid.

A groove 88, in which a sealing means is placed, is formed in the bottom face of the ring 83. A rubber ring can be used as the sealing means, but the groove 88 can also be filled with a suitable grease.

The axial seal can, if desired, also be supported by exerting a slight spring pressure on the housing not shown in FIG. 7. For this, a spring element can be fitted between the lower wall 15 (see FIG. 2) of the housing 14 and the corresponding wall of the probe head, for example one or more cup springs or a so-called sine spring.

The structure shown and described provides a completely closed probe head without inconvenient seams or crevices which are difficult to clean, while the transducer can still rotate freely, at least with little friction, together with a lens about the axis of rotation H2.

Figure 8:
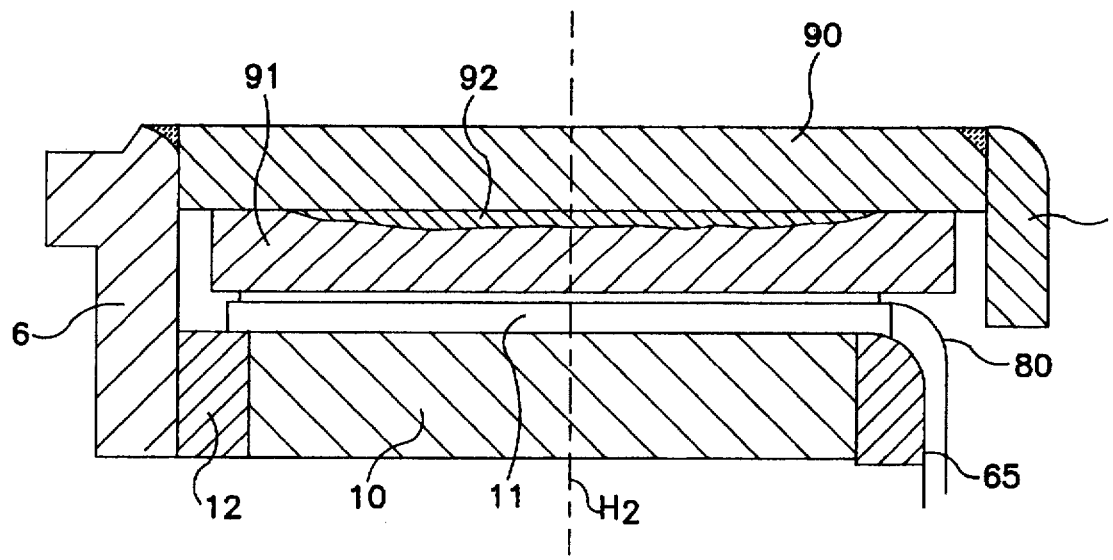
FIG. 8 shows schematically a second exemplary embodiment of a seal of a probe head of a probe according to the invention.

FIG. 8 shows a variant of FIG. 7, in which a cap 90 is glued at 84 directly in the aperture 9 without the interposition of a ring. A hard concave lens 91, which can be of the same type as the lens 81, and which is also provided with a flat filler 92, lies against the bottom side of the cap 90.

The fixed cap and the probe head, at least the front part thereof, can be made of the same material and can then be made, for example, of one piece. Between the cap 90 and the lens 91 a capillary gap is present, in which a liquid for reducing the friction, e.g. coupling oil, is present. Through the capillary action of the gap, the coupling oil does not flow away. If desired, an additional axial and/or radial seal can, however be used with the aid of O-rings and or with a grease-filled groove, as shown in FIG. 7. The lens can again be made of perspex or a hard epoxy resin. Like the cap 85 of FIG. 7, the cap 90 can preferably be made of a mechanically sturdy, but in acoustic respects aqueous material, so that in acoustic respects a good adjustment to human tissue is obtained. Suitable materials are e.g. methylpentene copolymers.

In the examplary embodiment shown in FIG. 8 also, the housing 14 can again if desired be under a slight upward pre-tension, so that the lens is held against the cap in all circumstances.

It is pointed out that, after the above, various modifications are obvious for the expert. For example, instead of the belt 17 a circular pulling cable, provided with a nipple falling into a cavity of the transducer housing, can be used. The belt 17 could also be replaced by yet another transmission mechanism such as a toothed rack which can be shifted by a pulling cable in the lengthwise direction, and which engages on a toothed wheel coupled directly or indirectly to the transducer housing. In that case it would be possible to make do with one pulling cable. Springs, which press the transducer housing back to a predetermined rest position can also be used.

Instead of a single flexible printed circuit board, as already stated, two or more flexible-printed circuit boards or one or more bunches of wires connected between the connectors 40, 41 and to the cables 30 to 33 could be used.

The belt 17 can also be made narrower and is preferably slightly recessed in a groove in the transducer housing.

The transducer, which in the example shown is essentially flat and hexagonal, can also be, for example, round or rectangular and slightly convex or even concave.

It is also pointed out that the probe described can also in principle be used for examination through body cavities other than the esophagus.

These and similar modifications are considered to fall within the scope of the invention.

We claim:

1. An endoscopic probe, which comprises:
   a probe head having an aperture and including a cylindrically-shaped transducer housing rotatably disposed therein,
   an ultrasonic transducer of the phase array type formed of a plurality of elongated transducer elements disposed within said transducer housing said ultrasonic transducer lying in plane substantially perpendicular to a rotatable axis of said transducer housing;

a lens having a concave cavity and a flat side, said flat side of said lens positioned on said ultrasonic transducer;

means for rotating said ultrasonic transducer in said transducer housing within a plane of said phase array of said ultrasonic transducer;

a loop-shaped flexible circuit board extending into said ultrasonic housing and connected to said plurality of elongated transducer elements;

a flexible tube connected to said probe head;

conductors extending through said flexible tube electrically connected to said flexible circuit board;

a cap member fixedly positioned within said aperture and comprised of a ring member sealed by a sealing substance to said aperture of said probe head in axial alignment with said ultrasonic transducer, said lens and cap member formed of an acoustically-compatible material and acoustically-coupled to one another; and a disc-shaped member of an ultrasonic sound transmitting material sealed within said ring member.

2. The endoscopic probe as defined in claim 1 wherein said concave cavity is provided with a flat filler.

3. The endoscopic probe as defined in claim 1 wherein said lens has a peripherally-formed groove for positioning an O-ring for contact with a wall surface of said probe head.

4. The endoscopic probe as defined in claim 1 wherein said ring member is formed with a cylindrically-shaped groove on a surface of contact with said lens for a sealing material to facilitate rotation of said lens with respect to said ring member.

5. The endoscopic probe as defined in claim 4 wherein said sealing material is grease.

6. The endoscopic probe as defined in claim 4 wherein said sealing material is rubber.

7. The endoscopic probe as defined in claim 1 wherein said sealing substance is glue.

8. The endoscopic probe as defined in claim 1 wherein said ring member is formed of a glass ceramic material.

9. The endoscopic probe as defined in claim 1 wherein said flexible printed circuit board in an unfolded state is substantially V-shaped forming two wing strips, each wing strip comprising an elongated part and a short transverse part having an end part of conductors.

10. The endoscopic probe as defined in claim 9 wherein each elongated part of each wing strip is comprised of two conductor tracks on either side of a fold line extending in a longitudinal direction of said wing strip.

11. The endoscopic probe as defined in claim 1 wherein said lens is an anamorphotic lens.

12. The endoscopic probe as defined in claim 1 wherein said lens is formed of a material selected from the group consisting of acrylic and epoxy resins.

13. The endoscopic probe as defined in claim 12 wherein said material is a hard epoxy resin.

14. The endoscopic probe as defined in claim 1 wherein an electrically non-conducting degassed fluid is disposed between said lens and said cap member.

15. The endoscopic probe as defined in claim 1 wherein said cap member is formed of a material in acoustic effects exhibits properties of an aqueous body.

16. The endoscopic probe as defined in claim 1 wherein an electrically non-conducting degassed fluid is disposed between said lens and said cap member.

17. The endoscopic probe as defined in claim 1 wherein said flexible circuit board extends into said transducer housing lying in a looped configuration therein having an end part of conductors connected to separate elongated transducer elements.

18. The endoscopic probe as defined in claim 17 wherein an opening in said transducer housing extends over a circular arc of about 180°.

19. The endoscopic probe as defined in claim 17 and further including a pin member fitted in said transducer housing for guiding therearound said flexible printed circuit board.

20. The endoscopic probe as defined in claim 19 and further including two pin members fitted in said transducer housing and extending substantially parallel to said longitudinal axis of said transducer housing on either side of said longitudinal axis of said probe head wherein said flexible printed circuit board is guided between said pin members.

21. The endoscopic probe as defined in claim 20 wherein said transducer housing includes a backing layer disposed in an electrically-insulating frame member in which is positioned said ultrasonic transducer.

22. The endoscopic probe as defined in claim 21 wherein said flexible printed circuit board is disposed beneath said backing layer of said transducer housing.

* * * * *